US008338386B2

(12) United States Patent
McLean et al.

(10) Patent No.: US 8,338,386 B2
(45) Date of Patent: Dec. 25, 2012

(54) PREVENTION/TREATMENT OF ICHTHYOSIS VULGARIS, ATOPY AND OTHER DISORDERS

(75) Inventors: William Henry Irwin McLean, Dundee (GB); Frances Jane Dorothy Smith, Dundee (GB)

(73) Assignee: University Court of the University of Dundee, Dundee (GB)

( * ) Notice: Subject to any disclaimer, the term of this patent is extended or adjusted under 35 U.S.C. 154(b) by 646 days.

(21) Appl. No.: 12/161,534

(22) PCT Filed: Jan. 17, 2007

(86) PCT No.: PCT/GB2007/000109
§ 371 (c)(1),
(2), (4) Date: Sep. 14, 2009

(87) PCT Pub. No.: WO2007/083094
PCT Pub. Date: Jul. 26, 2007

(65) Prior Publication Data
US 2010/0210578 A1    Aug. 19, 2010

(30) Foreign Application Priority Data

Jan. 18, 2006    (GB) .................................. 0600948.4

(51) Int. Cl.
*A61K 31/7105* (2006.01)
*A61K 31/7008* (2006.01)
*A61K 31/702* (2006.01)
*A61K 31/7036* (2006.01)
*C07H 5/06* (2006.01)
*C07H 21/02* (2006.01)
*C07H 15/20* (2006.01)
*C07H 15/22* (2006.01)
*C07H 15/222* (2006.01)
*C07H 15/224* (2006.01)
*C07H 15/226* (2006.01)
*C07H 15/228* (2006.01)
*C07H 15/232* (2006.01)
*C07H 15/234* (2006.01)

(52) U.S. Cl. ............. 514/53; 514/61; 514/62; 536/55.2; 536/24.1; 536/13.2; 536/13.3; 536/13.6; 536/13.7; 536/13.9; 536/14; 536/15; 536/16.2; 536/16.6

(58) Field of Classification Search .................. None
See application file for complete search history.

(56) References Cited

U.S. PATENT DOCUMENTS

| 6,143,502 | A  | 11/2000 | Grentzmann et al. |
| 2003/0124553 | A1 | 7/2003 | Ginger |
| 2005/0014835 | A1 | 1/2005 | Arakawa et al. |
| 2010/0017896 | A1 | 1/2010 | McLean et al. |

FOREIGN PATENT DOCUMENTS

| WO | WO01/44516 | 6/2001 |
| WO | WO 01/44516 | 6/2001 |
| WO | WO2004/010106 | 1/2004 |
| WO | WO 2004/010106 | 1/2004 |
| WO | WO2005/063261 | 7/2005 |
| WO | WO 2005/063261 | 7/2005 |

OTHER PUBLICATIONS

Merriam-Webster's Collegiate Dictionary, Tenth Edition, published 1998 by Merriam-Webster, Incorporated, p. 924.*
Silverman, "The Organic Chemistry of Drug Design and Drug Action" published 1992 by Academic Press, pp. 4-47.*
STN Database Descriptions, published 2006 by Chemical Abstracts Service, p. 52.*
Hennies et al., "Genetic and immunohistochemical detection of mutations inactivating the keratinocyte transglutaminase in patients with lamellar ichthyosis" Human Genetics (1998) vol. 102 pp. 314-318.*
Nirunsuksiri et al., "Reduced Stability and Bi-Allelic, Coequal Expression of Profilaggrin mRNA in Keratinocytes Cultured from Subjects With Ichthyosis Vulgaris" The Journal of Investigative Dermatology (1998) vol. 110 No. 6 pp. 854-861.*
Sybert et al., "Ichthyosis Vulgaris: Identification of a Defect in Synthesis of Filaggrin Correlated with an Absence of Keratohyaline Granules" The Journal of Investigative Dermatology (1985) vol. 84 pp. 191-194.*
Candi et al., 2005, "The Cornified Envelope: A Model of Cell Death in the Skin," *Nat Rev Mol Cell Biol*, vol. 6: p. 328-340.
Dale et al., 1985, "Filaggrin: A Keratin Filament Associated Protein," *Ann. NY Acad. Sci.*, vol. 455: p. 330-342.
Fleckman et al., 1987, "Keratinocytes Cultured From Subjects With Ichthyosis Vulgaris Are Phenotypically Abnormal," *J. Invest Dermatol*, vol. 88: p. 640-645.
Gan et al., 1990, "Organization, Structure, and Polymorphisms of the Human Profilaggrin Gene," *Biochemistry*, vol. 29: p. 9432-9440.
Hewett Duncan et al., 2005 "Lethal, Neonatal Ichthyosis With Increased Proteolytic Processing of Filaggrin in a Mouse Model of Netherton Syndrome," *Human Molecular Genetics*, vol. 14, No. 2: p. 335-346.
Ishida-Yamamoto et al., 1998, "Translocation of Profilaggrin N-Terminal Domain Into Keratinocyte Nuclei With Fragmented DNA in Normal Human Skin and Loricrin Keratoderma," *Lab Invest*, vol. 78: p. 1245-1253.
Judge et al., 2004, "Disorders of Keratinization," *Rook's Textbook of Dermatology*, vol. 2: p. 34.54-34.56.
Lane, P.W., 1972, "Two New Mutations in Linkage Group XVI of the House Mouse, Flaky Tail and Varitint-Waddler-J," *J Hered*, vol. 63: p. 135-140.
Listwan et al., 2004, "Keratin Bundling Proteins," *Methods Cell Biol*, vol. 78: p. 817-827.
Nirunsuksiri et al., 1995, "Decreased Profilaggrin Expression in Ichthyosis Vulgaris Is a Result of Selectively Impaired Post-transcriptional Control," *The Journal of Biological Chemistry*, vol. 270, No. 2: p. 871-876.

(Continued)

*Primary Examiner* — Eric S Olson
(74) *Attorney, Agent, or Firm* — Baker Botts LLP

(57) ABSTRACT

The present invention relates to the prevention/treatment of ichthyosis vulgaris (IV), atopy and potentially other disorders associated with loss-of-function mutations in the filaggrin gene sequence. The prevention/therapy is based on the use of agents which enable the host's translational machinery to read through a nonsense mutation found in a mutant allele of the filaggrin gene.

14 Claims, 8 Drawing Sheets

OTHER PUBLICATIONS

Nirunsuksiri et al., 1998, "Reduced Stability and Biallelic, Coequal Expression of Profilaggrin mRNA in Keratinocytes Cultured From Subjects With Ichyosis Vulgaris," *J. Invest Dermatol*, vol. 110: p. 851-861.

Palmer et al., 2006, "Common loss-of-function variants of the epidermal barrier protein filaggrin are a major predisposing factor for atopic dermatitis," *Nature Genetics*, vol. 38, No. 4: p. 441-446.

Panchal et al., 1999, "Partial Functional Correction of Xeroderma Pigmentosum Group A Cells by Suppressor tRNA," *Human Gene Therapy*, vol. 10, No. 13: p. 2216-2217.

Pena Penabad et al., 1998, "Differential Patterns of Filaggrin Expression in Lamellar Ichthyosis," *Br J Dermatol*, vol. 139: p. 958-964.

Presland et al., 1997, "Evidence for Specific Proteolytic Clevage of the N-Terminal Domain of Human Profilaggrin During Epidermal Differentiation," *J Invest Dermatol*, vol. 108: p. 107-178.

Presland et al., 2000, "Loss of Normal Profilaggrin and Filaggrin in Flaky Tail (ft/ft) Mice: An Animal Model for the Filaggrin-Deficient Skin Disease Ichtyosis Vulgaris," *J Invest Dermatol*, vol. 115: p. 1072-1081.

Rothnagel et al., 1994, "Characterization of the Mouse Loricrin Gene: Linkage With Profilaggrin and the Flaky Tail and Soft Coat Mutant Loci on Chromosome 3," *Genomics*, vol. 23: p. 450-456.

Smith Frances et al., 2006, "Loss-of-Function Mutations in the Gene Encoding Filaggrin Cause Ichthyosis Vulgaris," *Nature Genetics*, vol. 38, No. 3: p. 337-342.

Steinert et al., 1981, "Characterization of a Class of Cationic Proteins That Specifically Interact With Intermediate Filaments," *Proc Natl Acad Sci*, vol. 78: p. 4097-4101.

Sybert et al., 1985, "Ichthyosis Vulgaris: Identification of a Defect in Synthesis of Filaggrin Correlated With an Absence of Keratohyaline Granules," *J Invest Dermatol*, vol. 84: p. 191-194.

Wells et al., 1966, "Clinical Features of Autosomal Dominant and Sex-linked Ichthyosis in an English Population," *Br Med*, vol. 1: p. 947-949.

U.S. Appl. No. 12/097,493, Sep. 2, 2011 Non-Final Office Action.

U.S. Appl. No. 12/097,493, Jun. 9, 2011 Response to Non-Final Office Action.

U.S. Appl. No. 12/097,493, Dec. 9, 2010 Non-Final Office Action.

Hirshhorn et al., "A comprehensive review of genetic association studies", *Genetics in Medicine*, 4(2): 45-61, Mar./Apr. 2002.

Erichsen et al., "SNPs in cancer research and treatment", *British Journal of Cancer*, 90: 747-751, 2004.

Rugg et al., "DNA based prenatal testing for the skin blistering disorder epidermolysis bullosa simplex", *Prenatal Diagnosis*, 20: 371-377, 2000.

Ginger et al., "Filaggrin repeat number polymorphism is associated with a dry skin pheotype", *Arch Dermatol Res.*, 297: 235-241, 2005.

U.S. Appl. No. 12/097,493, May 2, 2012 Final Office Action.

* cited by examiner

Figure 2:

*(a) Normal sequence with translation*

```
5'C ATG GGA TCG CAC CAC GAG CAG GCA CGA GAC AGC TCC AGG CAT TCA GC 3'
    M   G   S   H   H   E   Q   A   R   D   S   S   R   H   S   A
```

Bases underlined are identical in wild-type *FLG*.
Bold = *FLG* codon 501.

Sense oligo
R501.F  5' CATGGGATCGCACCACGAGCAGGCACGAGACAGCTCCAGGCATTCAGC 3'

Antisense oligo
R501.R  5' CATGGCTGAATGCCTGGAGCTGTCTCGTGCCTGCTCGTGGTGCGATCC 3'

Double-stranded cassette

```
5' CATGGGATCGCACCACGAGCAGGCACGAGACAGCTCCAGGCATTCAGC    3'
3'     CCTAGCGTGGTGCTCGTCCGTGCTCTGTCGAGGTCCGTAAGTCGGTAC    5'
```

*(b) R501X version with translation*

Sense
```
5'C ATG GGA TCG CAC CAC GAG CAG GCA TGA GAC AGC TCC AGG CAT TCA GC 3'
    M   G   S   H   H   E   Q   A   X
```

Bases underlined are identical in R501X mutant allele of *FLG*.
Bold = *FLG* codon 501.

Sense oligo
X501.F  5' CATGGGATCGCACCACGAGCAGGCATGAGACAGCTCCAGGCATTCAGC 3'

Antisense oligo
X501.R  5' CATGGCTGAATGCCTGGAGCTGTCTCATGCCTGCTCGTGGTGCGATCC 3'

Double-stranded cassette

```
5' CATGGGATCGCACCACGAGCAGGCATGAGACAGCTCCAGGCATTCAGC    3'
3'     CCTAGCGTGGTGCTCGTCCGTACTCTGTCGAGGTCCGTAAGTCGGTAC    5'
```

Figure 3

```
Primer TR3.F
|    10        20        30        40        50
[CGATGCAGACAATATGCAGA]ATTTTAGCATCTTTTAGATGCCATAAACTC
 GCTACGTCTGTTATACGTCTTAAAATCGTAGAAAATCTACGGTATTTGAG 60        70        80        90       100
 CGCTTCTTCTGCCTTGGGAGTCAGAACAAACGACTTTTCTCTCCAAGGAG
 GCGAAGAAGACGGAACCCTCAGTCTTGTTTGCTGAAAAGAGAGGTTCCTC 110       120       130       140       150
 TAGTTATATTACCACAAGACTAAAATAATTGTCGATACCAACCGTTTATA
 ATCAATATAATGGTGTTCTGATTTTATTAACAGCTATGGTTGGCAAATAT 160       170       180       190       200
 AATCCCGATTCTGTGGCCCCAAATATCCCACCTAATCTAAAGTTTTCATT
 TTAGGGCTAAGACACCGGGGTTTATAGGGTGGATTAGATTTCAAAAGTAA 210       220       230       240       250
 TTCTCATTGGCGAAAACACGGGCGCTGTAGATGCCAACACGGGGGGTTGG
 AAGAGTAACCGCTTTTGTGCCCGCGACATCTACGGTTGTGCCCCCCAACC 260       270       280       290       300
 AGGGGGCGGGTGGGGGGAAGCTCGTTTTATTTTCTAAGTATTGCAGCAAC
 TCCCCCGCCCACCCCCCTTCGAGCAAAATAAAAGATTCATAACGTCGTTG TR3 gene                    Anticodon loop
        310      |320       330       340       350
 AACGGAACTGCGGGG[ACCACGTGGCCTAATGGATAAGGCGTCTGACTTC
 TTGCCTTGACGCCCC]TGGTGCACCGGATTACCTATTCCGCAGACTGAAG]

A G351A mutation
|    360       370       380       390       400
[G]GATCAGAAGATTGAGGGTTCGAATCCCTTCGTGGTTA]GTGGGGTTCGT
 CCTAGTCTTCTAACTCCCAAGCTTAGGGAAGCACCAATT]CACCCCAAGCA 410       420       430       440       450
 TTTCGGGCATGAAAATTTTATTACCCATTTCATTCCAAGAAAAAAATAAA
 AAAGCCCGTACTTTTAAAATAATGGGTAAAGTAAGGTTCTTTTTTTATTT 460       470       480       490       500
 TCATACACTCTCTGGGTTTTCTGAATCCTTTTTTTCTTCCATCTCCTCTC
 AGTATGTGAGAGACCCAAAAGACTTAGGAAAAAAAGAAGGTAGAGGAGAG 510       520       530       540       550
 CTTTAAAGGGAAGAAGGAGACATTCTCAAAGGCCTTAGGAGAACAAGTGA
 GAAATTTCCCTTCTTCCTCTGTAAGAGTTTCCGGAATCCTCTTGTTCACT 560       570       580       590       600
 CAGAGTGAAGAAAGACTGGAAAGTCAAAACTGAAATACAGCCATCTACTA
 GTCTCACTTCTTTCTGACCTTTCAGTTTTGACTTTATGTCGGTAGATGAT 610       620       630       640       650
 CTTTGGAGCTGTCAGGTTCTCCCCAAGTTTGGATTTTAAGCACCTGCGTT
 GAAACCTCGACAGTCCAAGAGGGGTTCAAACCTAAAATTCGTGGACGC[AA]

Primer TR3.R
        660       |
 TCGGTTTTGTAGGCTTAG
[AGCCAAAACATCCGAATC]
```

Figure 4

```
Primer TR4B.F
|       10        20        30        40        50
GACTTCTGGGTGGGCTCTCCCTGCGGAACGCGCGAACCAAAGGCCAACCT
CTGAAGACCCACCCGAGAGGGACGCCTTGCGCGCTTGGTTTCCGGTTGGA 60        70        80        90       100
CCCCTTCTCAAGGAGCAGGTGGATTGGTCCCGAGCTAGCTGGTGGGCGGA
GGGGAAGAGTTCCTCGTCCACCTAACCAGGGCTCGATCGACCACCCGCCT TR4B gene
        110       120       130       140       |150
GGTGACGTTTTTATAAGTTGCTCAAGAGACGGTAACAACCGACGGGCCGC
CCACTGCAAAAATATTCAACGAGTTCTCTGCCATTGTTGGCTGCCCGGCG Anticodon loop A  G180A mutation
                            |
        160       170       180       190       200
GTGGCCTAATGGATAAGGCGTCTGACTTCGGATCAGAAGATTGCAGGTTC
CACCGGATTACCTATTCCGCAGACTGAAGCCTAGTCTTCTAACGTCCAAG 210       220       230       240       250
GAGTCCTGCCGCGGTCGAAGGGAGGTTATGATTAACTTTTAGTTTATTCC
CTCAGGACGGCGCCAGCTTCCCTCCAATACTAATTGAAAATCAAATAAGG 260       270       280       290       300
TCCCTCAGGAACGAAGTATTGGGACAATGTGAACGTAGTCGCCGCCGATT
AGGGAGTCCTTGCTTCATAACCCTGTTACACTTGCATCAGCGGCGGCTAA 310       320       330       340       350
CCCACCGCACTTCAAAGATGTGGGAACGCCAAGATCCGCGGAAGTAACCA
GGGTGGCGTGAAGTTTCTACACCCTTGCGGTTCTAGGCGCCTTCATTGGT 360       370       380       390       400
CGCCCAGCAAGTCCCTGCGAGATTGCCCGCCTACGTGTCTCAGCGGAGGC
GCGGGTCGTTCAGGGACGCTCTAACGGGCGGATGCACAGAGTCGCCTCCG 410       420       430       440       450
ACATTTCTAAAATGTACCAGGTCTCTCGCACCCCGACGCAGGTGGAGGAA
TGTAAAGATTTTACATGGTCCAGAGAGCGTGGGGCTGCGTCCACCTCCTT Primer TR4B.R
        460    |
AGTGGAGAGGGAGGG
TCACCTCTCCCTCCC
```

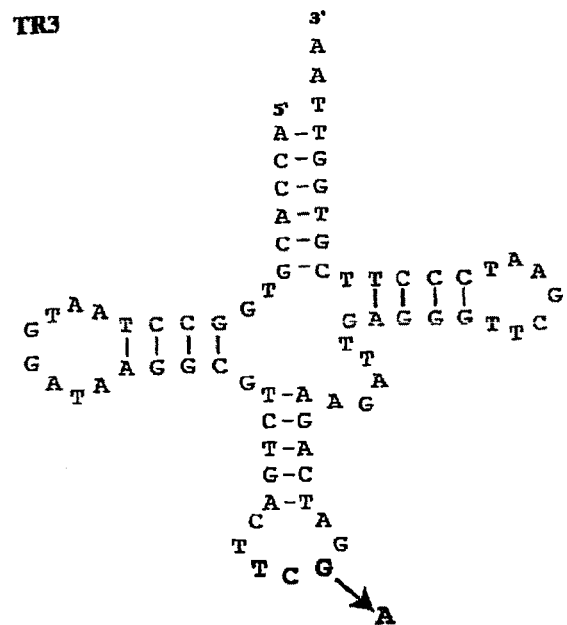
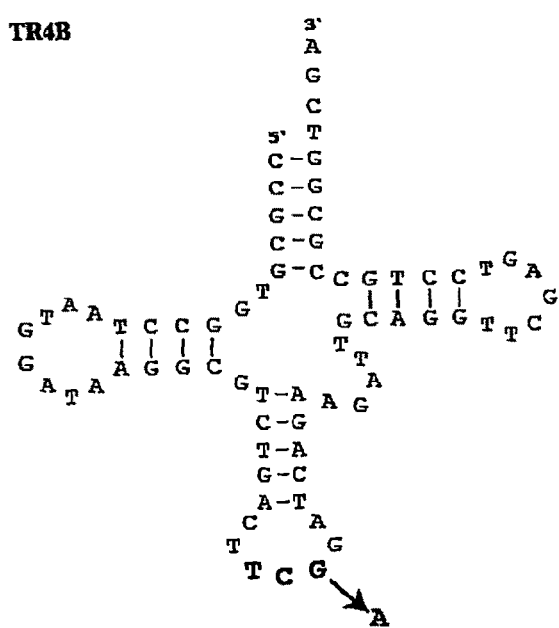
Figure 5

Figure 6
(a)
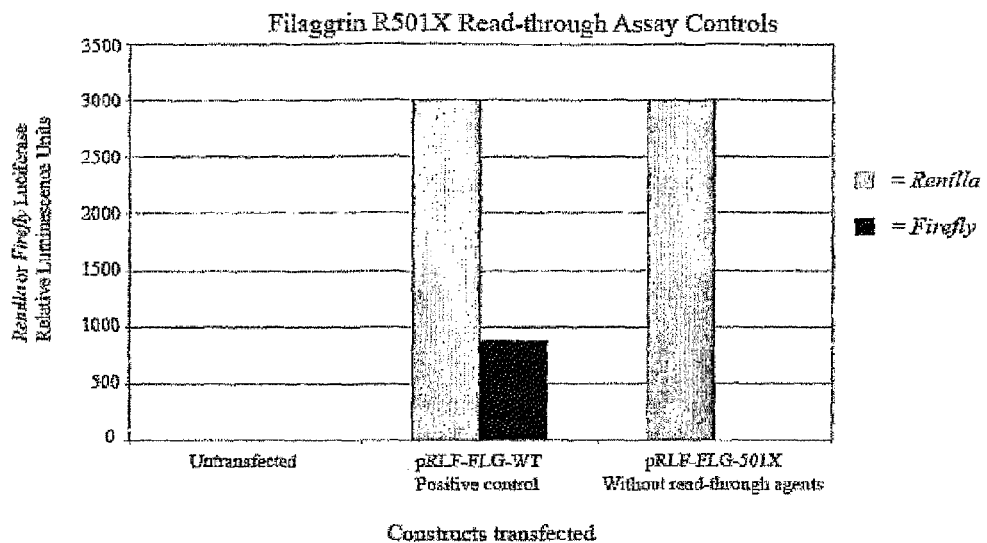
(b)
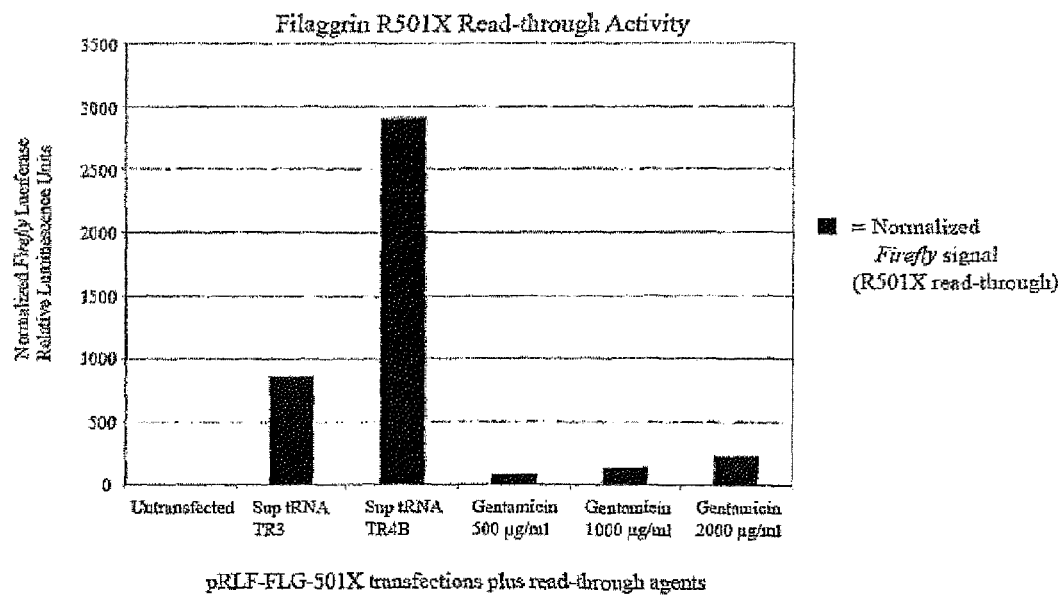

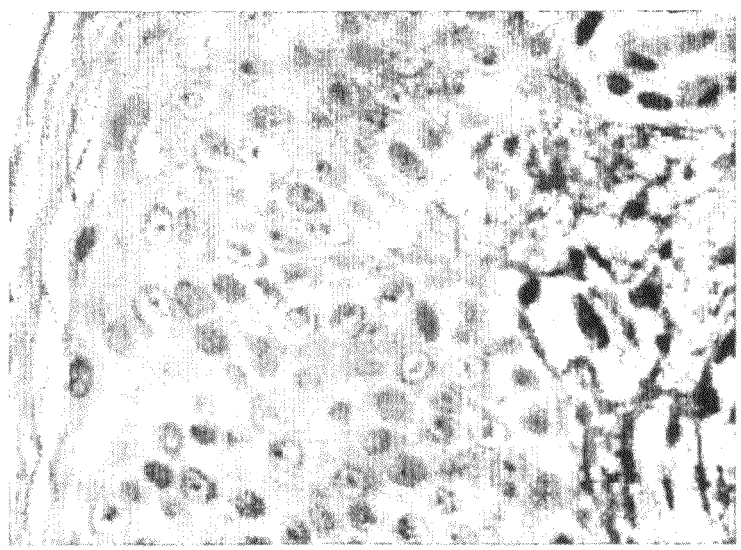
Figure 8

```
                         SEQUENCE LISTING

<160> NUMBER OF SEQ ID NOS: 20

<210> SEQ ID NO 1
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 1
aggcattcag ccagggtcac cgacgcc                                         27

<210> SEQ ID NO 2
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 2
ggcgtcggtg accctggctg aatgcct                                         27

<210> SEQ ID NO 3
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 3
tcaaaaatga acaaattcta gagcggcc                                        28

<210> SEQ ID NO 4
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 4
ggccgctcta gaatttgttc attttttga                                       28

<210> SEQ ID NO 5
<211> LENGTH: 20
<212> TYPE: DNA
<213> ORGANISM: Artificial sequence
<220> FEATURE:
```

-continued

<223> OTHER INFORMATION: Synthetic oligonucleotide

<400> SEQUENCE: 5
cgatgcagac aatatgcaga                                        20

<210> SEQ ID NO 6
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 6
ctaagcctac aaaaccgaaa                                        20

<210> SEQ ID NO 7
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 7
gacttctggg tgggctctcc                                        20

<210> SEQ ID NO 8
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 8
ccctccctct ccactttcct                                        20

<210> SEQ ID NO 9
<211> LENGTH: 48
<212> TYPE: DNA
<213> ORGANISM: Artificial sequence
<220> FEATURE:
<223> OTHER INFORMATION: Synthetic oligonucleotide

<400> SEQUENCE: 9
catgggatcg caccacgagc aggcacgaga cagctccagg cattcagc         48

<210> SEQ ID NO 10
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 10

Met Gly Ser His His Glu Gln Ala Arg Asp Ser Ser Arg His Ser Ala
1               5                   10                  15

<210> SEQ ID NO 11
<211> LENGTH: 48
<212> TYPE: DNA
<213> ORGANISM: Artificial sequence
<220> FEATURE:
<223> OTHER INFORMATION: Synthetic oligonucleotide

<400> SEQUENCE: 11
catgggatcg caccacgagc aggcatgaga cagctccagg cattcagc         48

```
<210> SEQ ID NO 12
<211> LENGTH: 9
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (9)..(9)
<223> OTHER INFORMATION: Xaa can be any naturally occurring amino acid

<400> SEQUENCE: 12

Met Gly Ser His His Glu Gln Ala Xaa
1               5

<210> SEQ ID NO 13
<211> LENGTH: 48
<212> TYPE: DNA
<213> ORGANISM: Artificial sequence
<220> FEATURE:
<223> OTHER INFORMATION: Synthetic oligonucleotide

<400> SEQUENCE: 13
catggctgaa tgcctggagc tgtctcgtgc ctgctcgtgg tgcgatcc              48

<210> SEQ ID NO 14
<211> LENGTH: 48
<212> TYPE: DNA
<213> ORGANISM: Artificial sequence
<220> FEATURE:
<223> OTHER INFORMATION: Synthetic oligonucleotide

<400> SEQUENCE: 14
catggctgaa tgcctggagc tgtctcatgc ctgctcgtgg tgcgatcc              48

<210> SEQ ID NO 15
<211> LENGTH: 667
<212> TYPE: DNA
<213> ORGANISM: Artificial sequence
<220> FEATURE:
<223> OTHER INFORMATION: Synthetic oligonucleotide

<400> SEQUENCE: 15
cgatgcagac aatatgcaga attttagcat cttttagatg ccataaactc cgcttcttct      60
gccttgggag tcagaacaaa cgactttttct ctccaaggag tagttatatt accacaagac    120
taaaataatt gtcgatacca accgtttata aatcccgatt ctgtggcccc aaatatccca    180
cctaatctaa agtttcatt ttctcattgg cgaaaacacg ggcgctgtag atgccaacac    240
ggggggttgg aggggcggg tggggggaag ctcgttttat tttctaagta ttgcagcaac    300 aacgaactg cggggacca cgtggctaat ggataaggcg tctgacttcg gatcagaaga    360
ttgagggttc gaatcccttc gtggttaagt ggggttcgtt ttcgggcatg aaaattttat    420
tacccatttc attccaagaa aaaataaat catacactct ctgggttttc tgaatccttt    480
ttttcttcca tctcctctcc tttaaaggga agaaggagac attctcaaag gccttaggag    540
aacaagtgac agagtgaaga aagactggaa agtcaaaact gaaatacagc catctactac    600
tttggagctg tcaggttctc cccaagtttg gattttaagc acctgcgttt cggttttgta    660
ggcttag                                                              667

<210> SEQ ID NO 16
<211> LENGTH: 668
<212> TYPE: DNA
<213> ORGANISM: Artificial sequence
<220> FEATURE:
```

<223> OTHER INFORMATION: Synthetic oligonucleotide

<400> SEQUENCE: 16

```
ctaagcctac aaaaccgaaa cgcaggtgct taaaatccaa acttggggag aacctgacag    60
ctccaaagta gtagatggct gtatttcagt tttgactttc cagtctttct tcactctgtc   120
acttgttctc ctaaggcctt tgagaatgtc tccttcttcc ctttaaagga gaggagatgg   180
aagaaaaaaa ggattcagaa aacccagaga gtgtatgatt ttatttttt cttggaatga    240
aatgggtaat aaaattttca tgcccgaaaa cgaaccccac ttaaccacga agggattcga   300
accctcaatc ttctgatccg aagtcagacg ccttatccat taggccacgt ggtccccgc   360
agttccgttg ttgctgcaat acttagaaaa taaaacgagc ttcccccac ccgccccctc   420
caaccccccg tgttggcatc tacagcgccc gtgttttcgc caatgagaaa atgaaaactt   480
tagattaggt gggatatttg gggccacaga atcgggattt ataaacggtt ggtatcgaca   540
attattttag tcttgtggta atataactac tccttggaga gaaaagtcgt ttgttctgac   600
tcccaaggca gaagaacgga gtttatggca tctaaaagat gctaaaattc tgcatattgt   660
ctgcatcg                                                            668
```

<210> SEQ ID NO 17
<211> LENGTH: 515
<212> TYPE: DNA
<213> ORGANISM: Artificial sequence
<220> FEATURE:
<223> OTHER INFORMATION: Synthetic oligonucleotide

<400> SEQUENCE: 17

```
gacttctggg tgggctctcc ctgcggaacg cgcgaaccaa aggccaacct ccccttctca    60
aggagcaggt ggattggtcc cgagctagct ggtgggcgga ggtgacgttt ttataagttg   120
ctcaagagac ggtaacaacc gacgggccgc gtggcctaat ggataaggcg tctgacttcg   180
gatcagaaga ttgcaggttc gagtcctgcc gcggtcgaag ggaggttatg attaactttt   240
agtttattcc tccctcagga acgaagtatt gggacaatgt gaacgtagtc gccgccgatt   300
cccaccgcac ttcaaagatg tgggaacgcc aagatccgcg gaagtaacca cgcccagcaa   360
gtccctgcga gattgcccgc ctacgtgtct cagcggaggc acatttctaa aatgtaccag   420
gtctctcgca ccccgacgca ggtggaggaa acatttctaa aatgtaccag gtctctcgca   480
ccccgacgca ggtggaggaa agtggagagg gaggg                              515
```

<210> SEQ ID NO 18
<211> LENGTH: 464
<212> TYPE: DNA
<213> ORGANISM: Artificial sequence
<220> FEATURE:
<223> OTHER INFORMATION: Synthetic oligonucleotide

<400> SEQUENCE: 18

```
ccctccctct ccactttcct ccacctgcgt cggggtgcga gagacctggt acattttaga    60
aatgtgcctc cgctgagaca cgtaggcggg caatctcgca gggacttgct gggcgtggtt   120
acttccgcgg atcttggcgt tcccacatct ttgaagtgcg gtgggaatcg gcggcgacta   180
cgttcacatt gtcccaatac ttcgttcctg agggaggaat aaaactaaaag ttaatcataa   240
cctcccttcg accgcggcag gactcgaacc tgcaatcttc tgatccgaag tcagacgcct   300
tatccattag gccacgcggc ccgtcggttg ttaccgtctc ttgagcaact tataaaaacg   360
tcacctccgc ccaccagcta gctcgggacc aatccacctg ctcctgagaa ggggaggttg   420
```

```
gcctttggtt cgcgcgttcc gcagggagag cccacccaga agtc                      464

<210> SEQ ID NO 19
<211> LENGTH: 73
<212> TYPE: DNA
<213> ORGANISM: Artificial sequence
<220> FEATURE:
<223> OTHER INFORMATION: Synthetic oligonucleotide

<400> SEQUENCE: 19
accacgtggc ctaatggata aggcgtctga cttcrgatca gaagattgag ggttcgaatc      60
ccttcgtggt taa                                                        73

<210> SEQ ID NO 20
<211> LENGTH: 72
<212> TYPE: DNA
<213> ORGANISM: Artificial sequence
<220> FEATURE:
<223> OTHER INFORMATION: Synthetic oligonucleotide

<400> SEQUENCE: 20
ccgcgtggcc taatggataa ggcgtctgac ttcrgatcag aagattgcag gttcgagtcc      60
tgccgcggtc ga                                                         72
```

PREVENTION/TREATMENT OF ICHTHYOSIS VULGARIS, ATOPY AND OTHER DISORDERS

CROSS-REFERENCE TO RELATED APPLICATIONS

This application is a national phase of International Application PCT/GB2007/000109, filed Jan. 17, 2007, which claims priority of Great Britian Application No. GB0600948.4, filed on Jan. 18, 2006, both of which are herein incorporated by reference.

FIELD OF THE INVENTION

The present invention relates to the prevention/treatment of ichthyosis vulgaris (IV), atopy and potentially other disorders associated with loss-of-function mutations in the filaggrin gene sequence. The prevention/therapy is based on the use of agents which enable the host's translational machinery to read through a nonsense mutation found in a mutant allele of the filaggrin gene.

SEQUENCE LISTING

The specification further incorporates by reference the Sequence Listing submitted herewith via EFS on Apr. 22, 2010. Pursuant to 37 C.F.R. §1.52(e)(5), the Sequence Listing text file, identified as 0793540103seqlist.txt, is 7,522 bytes and was created on Apr. 22, 2010. The Sequence Listing, electronically filed herewith, does not extend beyond the scope of the specification and thus does not contain new matter.

BACKGROUND OF THE INVENTION

Ichthyosis vulgaris (IV; OMIM #146700) is the most common inherited disorder of keratinisation and one of the most frequent single gene disorders in humans. The most widely cited incidence figure is 1 in 250 based on a survey of 6051 healthy English schoolchildren[1]. The association of IV with the atopic diathesis is well established; 37-50% of people with IV have atopic diseases, in particular atopic dermatitis (eczema)[1,15] and conversely around 8% of atopic dermatitis patients have classical features of IV[1,16].

The phenotypic characteristics of IV include palmar hyperlinearity, keratosis pilaris and a fine scale most markedly seen over the lower abdomen, arms and legs[2]. Filaggrin (filament aggregating protein) is important in the formation of the stratum corneum[3,5]. Keratohyalin granules in the granular layer of interfollicular epidermis are predominantly composed of the 400 kDa protein profilaggrin. Following a short, unique N-terminal domain, most of the profilaggrin molecule consists of 10-12 repeats of the 324 amino acid filaggrin sequence[6]. Upon terminal differentiation of granular cells, profilaggrin is proteolytically cleaved into ~37 kDa filaggrin peptides and the N-terminal domain containing an S100-like calcium binding domain. Filaggrin rapidly aggregates the keratin cytoskeleton, causing collapse of the granular cells into flattened anuclear squames. This condensed cytoskeleton is cross-linked by transglutaminases during formation of the cornified cell envelope (CCE). The CCE is the outermost barrier layer of the skin which not only prevents water loss but also impedes the entry of allergens and infectious agents[7]. Filaggrin is therefore a key protein in facilitating epidermal differentiation and maintaining barrier function.

Immunoblotting studies have shown that filaggrin protein was absent or markedly reduced in IV patients' skin and/or keratinocytes[8-10]. In addition, decreased filaggrin mRNA has been demonstrated in some individuals with IV[11]. A recessive mouse mutant, flaky tail (ft), bears the histological and ultrastructural hallmarks of human IV[12] and strong genetic linkage has been obtained to the murine filaggrin locus (FLG)[17, 18]. Although biochemical analysis has shown defective profilaggrin processing in ft/ft homozygotes[12], any genomic mutation in the FLG gene has not hitherto been identified.

The present inventors have discovered certain loss of function mutations in the gene encoding filaggrin and that the consequence reduction/loss of filaggrin is associated with the development of IV and other disorders such as atopic dermatitis (eczema), asthma, psoriasis and/or allergies.—This work is the subject of several papers which are in press (Smith F. J. D. et al., 2006; Palmer C. N. A. et al., 2006) and a co-pending patent application GB0525492.5.

Apart from potential treatment by gene therapy applications, it would be desirable if IV could be treated using small molecule drugs designed to overcome at least some of the identified filaggrin mutations.

Thus, it is amongst the objects of the present invention to provide means for preventing and/or treating IV and other associated disorders.

SUMMARY OF THE INVENTION

The present invention is based in part on work by the inventors in relation to the ability of certain agents to allow read through of loss-of-function mutations in the filaggrin gene.

In a first aspect the present invention provides use of an agent which is capable of enabling read through of a loss-of-function mutation in a filaggrin gene for the manufacture of a medicament for treating IV and/or associated diseases.

In a further aspect there is provided a method of treating IV and/or other associated diseases comprising the step of administrating to a subject an agent which is capable of enabling read-through of a loss-of-function mutation in a filaggrin gene.

It will be appreciated that the present invention enables treatment of IV and/or to treating an animal subject, especially a human subject who is predisposed to developing IV. Additionally, due to an association of IV, in severe or mild forms, with other diseases, the treatment may be used on a subject who is likely to be predisposed or suffering from atopic dermatitis (eczema), asthma, psoriasis or allergies, such as of a contact type allergy and food allergies (for example, peanut allergy). With regards to skin conditions, low levels of filaggrin expression may lead to development of mild and/or sub-clinical disease. In this manner, the present invention may also relate to the prevention and/or treatment of said mild and/or sub-clinical forms of disease. Indeed, many skin conditions go undiagnosed and as such treatments may be considered more as a cosmetic treatment. Thus the present invention also extends to any such cosmetic therapies.

The loss of function mutations which may be overcome are generally nonsense mutations. Such mutations are typically single base modifications which result in the generation of a premature stop codon (i.e. TGA, TAG or TAA). Although the present inventors have identified a number of mutations in the filaggrin gene, which lead to a loss-of-function, one in particular leads to an in-frame generation of a premature stop codon. This mutation is a 1-base substitution at position 1501 of the FLG gene. The mutation is 1501C>T (numbering from initiating ATG), which results in the substitution of a cytidine by a thymidine and a corresponding amino acid change at position 501 of an arginine to a stop codon (R501X). As this mutation occurs in the first filaggrin repeat and results in the generation of a stop codon, no functional copies of the filaggrin peptide are produced. Although, the inventors have identified other mutations in the filaggrin gene, this has so far been observed as the most common in European Caucasian populations and it is overcoming of this mutation which is the preferred aspect of the present invention.

The subject may be any subject requiring to be treated, prophylactically or therapeutically and may suitably be a newborn or even a foetus. The subject may however be at any stage of life, and therefore includes neonates, children and adults.

There are a number of known agents which are able to induce the read-through of nonsense mutations. One class of agents are certain aminoglycoside antibiotics, including gentamicin, paromomycin, neomycin and tobramycin (Bidou L. et al., Gene Therapy 11:619-627, 2004; Howard M T., et al. Ann Neurol, 55:422-426, 2004).

Another class of agents including negamycin, is described in US2005/0014835 which is hereby incorporated by reference. Finally mutated tRNAs may be generated as nonsense mutation suppressors. These are generated from mutant tRNA genes that result in the generation of tRNAs that have anticodons altered so that they have the ability to read through codons produced by nonsense mutations. This is described, for example, in Panchal R G et al., Human Gene Therapy, 10:2209-2219 (1999).

In addition to the identified agents mentioned above, there may be other suitable mutation suppressors and the present invention also provides a method of identifying such suppressors.

Thus, in a further aspect there is provided a method of testing an agent for its ability to read-through a nonsense mutation comprising the steps of:

a) providing a mutant filaggrin gene/reporter gene construct;

b) contacting a test agent with said construct; and c) detecting whether or not the test agent is capable of effecting read-through of the mutant filaggrin gene and expression of a reporter gene.

Any suitable identified agents may be of use in treating IV and/or other associated diseases mentioned herein, or indeed any disease/genetic condition caused by a nonsense mutation.

It will be appreciated that the construct will be under control of appropriate transcription control elements such as promoter and terminator sequences. Moreover, a filaggrin nucleic acid sequence comprising an internal nonsense sequence will be present in the construct. It is not necessary to use the entire filaggrin nucleic acid sequence, only a portion is required. Conveniently, the filaggrin nucleic acid sequence may be 10-1000 bp in length, more preferably 15-200 bp in length.

A typical mutant filaggrin gene/reporter gene construct comprises a 5' mutant filaggrin nucleic acid sequence joined in-frame to a 3' reporter gene sequence. In this manner in order for any expression of the reporter gene sequence to occur, there must be read-through nonsense/stop codon located within the 5' filaggrin sequence.

A preferred construct further comprises an additional positive control reporter gene 5' of the filaggrin sequence. As will be appreciated all sequences are joined in-frame with one another. For such a construct, the 5' positive control reporter is provided so that a user can ensure the construct is functioning appropriately. If no read-through of the filaggrin gene occurs, only the positive reporter will provide a detectable signal. However, if read-through of the filaggrin sequence occurs, both the positive control reporter and the reporter gene 3' of the filaggrin sequence will provide detectable signals. Alternatively, the positive reporter may present in the construct under control of a separate promoter or, the positive reporter may be encoded by a separate plasmid which is co-transfected Suitable reporter genes for use of the reporter gene or positive control reporter gene are well known to the skilled addressee and include, for example, a luciferase gene, β-galactosidase gene, fluorescent genes, such as green fluorescent protein or the like, chloramphenicol acetyltransferase, β-glucuronidase and the like. Moreover, different versions of a particular gene may be obtained from different species of organism.

A particularly preferred construct comprises the renilla luciferase gene as a positive control reporter, a mutant filaggrin nucleic acid sequence and the firefly luciferase gene as the reporter gene, under appropriate transcriptional control using, for example, the HSV-TK promoter and SV40-polyA terminator signal, as schematically shown in FIG. 1. However, many other suitable constructs can be envisaged and the reporters may be reporters which only allow cells to survive in certain growth medium if the reporter is expressed.

Detection of expression of any particular reporter can be carried out by techniques well known to the skilled reader.

Following a first round of screening, it may be appropriate to test any possible useful agent, by testing the agent on a cell or cell-line obtained from a patient suffering from a disease associated with a nonsense mutation in order to ascertain/confirm that the agent is able to cause read-through of the mutation.

It will be appreciated that the method may be carried out in cell based or cell-free systems known in the art.

The present invention will now be further described by way of example and with reference to the Figures which show:

FIG. 1 shows a construct for assay of filaggrin nonsense mutation read-through agents. A: TAA stop codon mutated out of R-Luc in pRL-TK by 2 bp deletion & Xba I site put in-frame with FLG and f-Luc; B: FLG oligo cassette cloned into Nco I site of pSP-luc+NF; C: ATG codon mutated out of f-Luc to reduce "leaky" expression.

FIG. 2 shows FLG oligonucleotide cassettes for cloning into pSP-luc+;

FIG. 3 shows TR3 construct: human Arg(CGA) tRNA gene from chromosome 6p22.1;

FIG. 4 shows TR4B construct: human tRNA-Arg(TCG) gene from chromosome 15q26.1;

FIG. 5 shows the predicted secondary structures of TR3 and TR4B suppressor tRNAs showing mutated anticodon loops. The anticodon loop is shown in bold and the G>A mutation which allows this to pair with TGA codons is marked. Bases shown are predicted from DNA and do not account for post-transcriptional modiciations;

FIG. 6 shows read-through of the filaggrin R501X mutation (a) Epithelial cell line 293 was transiently transfected with pRLF-FLG-WT or pRLF-FLG-501X reporter plasmids. 48 hours after transfection, cells were lysed and luciferase was assayed using the Promega Dual-Luciferase assay system, according to the manufacturer's protocols.

Untransfected cells gave neither Renilla or Firefly signal. The positive control construct pRLF-FLG-WT, containing the wild-type filaggrin sequence, gave positive Renilla and Firefly signals. In contrast, the pRL-FLG-501X construct gave an equivalent Renilla signal but in the absence of any read-through agents, gave no detectable Firefly signal. This demonstrates that the pRLF-FLG-501X construct is not "leaky" and is therefore suitable for assay or read-through agents.

(b) The 293 cell-line was transiently transfected with pRLF-FLG-501X co-reporter containing a fragment of the human filaggrin gene carrying the R501X mutation cloned in frame between the Renilla and Firefly luciferase genes.

Read-through activity was measured as Firefly luciferase activity normalized against Renilla luciferase activity. Readings were done in quadruplicate and averaged.

Figure 7:
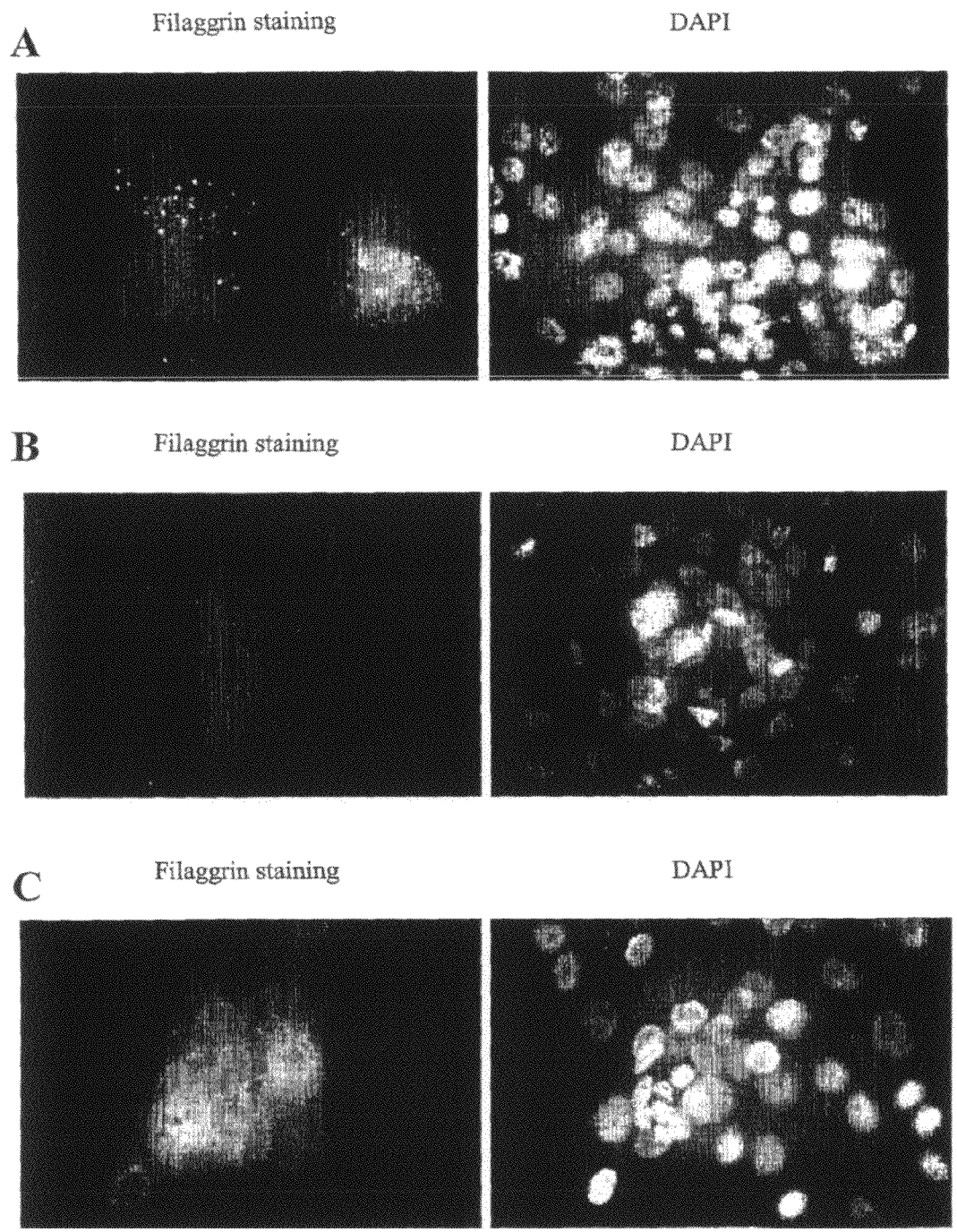

Suppressor tRNAs TR3 and TR4BsupTGA allow readthrough of filaggrin R501X nonsense mutation. Gentamicin allows read-through of the filaggrin R501X mutation in a dose-dependent manner;

FIG. 7 shows that gentamicin induces re:expression of filaggrin in keratinocytes from an ichthyosis vulgaris individual (FLG R501X homozygote).

Primary keratinocytes were grown in serum-free KGM and were induced to stratify (differentiate) by shifting from low (0.09 mM) to high-calcium medium (1.89 mM). Cultures were fixed using methanol/acetone and stained by indirect immunofluorescence using Novocastra monoclonal antibody 15C10 against the human filaggrin repeat sequence. Nucleic were counterstained using 1 mg/ml DAPI (4,6-diamidino-2-phenylindole); (a) normal control keratinocytes express filaggrin upon differentiation, (b) R501X homozygote keratinocytes do not express filaggrin upon differentiation, (c) R501X homozygote keratinocytes express filaggrin upon differentiation in presence of 600 μg/ml gentamicin (96 hrs incubation with drug); and FIG. 8 shows filaggrin expression from an R501X patient following gentamycin treatment. Incubation of skin biopsy material from an R501X homozygotet patient with marked ichthyosis vulgaris with 600 μg/ml gentamicin for 96 hours in organ culture restores filaggrin expression (arrows). Following incubation, biopsies were formalin-fixed, paraffin-embedded and processed for immunohistochemistry using Novocastra anti-human filaggrin repeat monoclonal antibody 15C10 with immunoperoxidase detection; A: Untreated biopsy; B: Gentamicin treatment
Methods and Results

EXAMPLE 1

Co-reporter Gene Construct for Assay of Readthrough Agents

Oligonucleotide cassettes corresponding to base numbers 1480-1523 of the human filaggrin gene, (FLG; numbering the coding sequence from the ATG initiation codon; Genbank accession number NM_002016.1), were cloned into the unique Nco I restriction site that spans the ATG codon of the firefly luciferase gene (f-Luc) in plasmid vector pSP-luc+NF (Promega). The oligo cassettes, shown in FIG. 2, had overhangs added corresponding to the cohesive ends of Nco I. These cassettes correspond to the region of the human FLG gene containing codon 501, the site of the common R501X mutation. Both wild-type and R501X mutant versions were made. Clones with the insert in the correct orientation were identified and verified by DNA sequencing. The ATG codon following insertion of the FLG cassette, i.e. the original initiation codon of the f-Luc gene, was mutated to an AGG arginine codon by site-directed mutagenesis with the following primers: FLmut1 5' AGG CAT TCA GCC AGG GTC ACC GAC GCC 3' and FLmut2 5' GGC GTC GGT GAC CCT GGC TGA ATG CCT 3' (Stratagene QuikChange system). This was to prevent possible use of the original initiation codon, which might lead to "leaky" expression of firefly luciferase even in the presence of the FLG cassette containing a TGA or other stop codon. Clones were verified by DNA sequencing. These clones were designated pSP-R501 and pSP-X501, corresponding to the wild-type and mutant versions, respectively.

The TAA termination codon of the Renilla luciferase gene (R-Luc) in plasmid vector pRL-TK (Promega) was mutated out by deletion of 2 bp (TA). This was done using by site-directed mutagenesis with the following primers: pRL.M1 5' TCA AAA ATG AAC AAA TTC TAG AGC GGC C 3' and pRL.M2 5' GGC CGC TCT AGA ATT TGT TCA TTT TTG A 3' (Stratagene QuikChange system). The mutated clone (designated pRL-M1) was fully sequenced.

Figure 1:
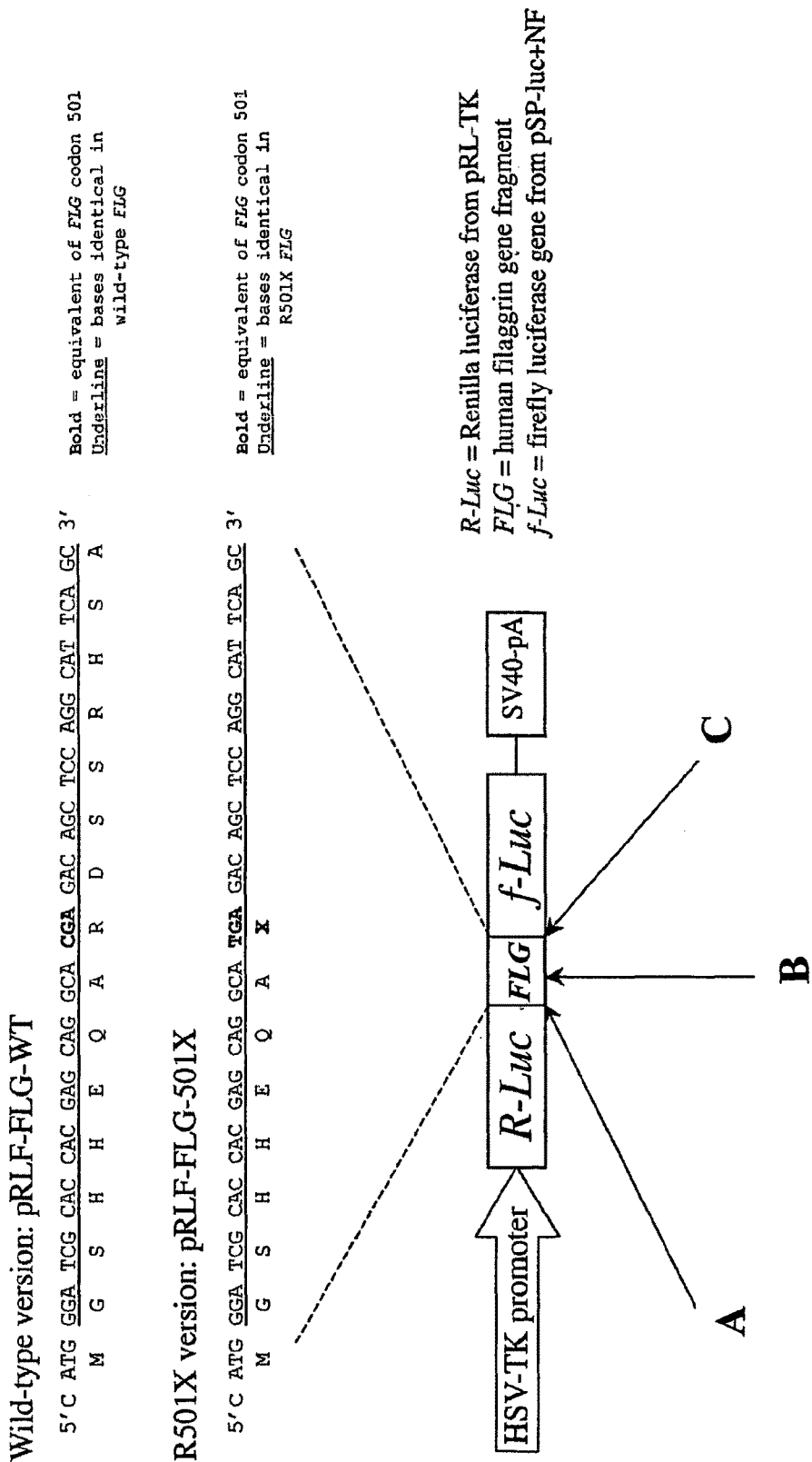

To make the finished co-reporter constructs, Nhe I-Xba I fragments comprising the entire FLG-f-Luc fusion gene were excised from pSP-R501 and pSP-X501. These were cloned into the unique Xba I site of pRL-M1, which was possible since Nhe I and Xba I have compatible cohesive ends. Wildtype and R501X mutant clones with the correct orientation were selected by DNA sequencing. The wild-type and R501X mutant co-reporter constructs were designated as pRLF-FLG-WT and pRLF-FLG-501X, respectively (FIG. 1).

EXAMPLE 2

Generation of Human Suppressor tRNA Genes for TGA Nonsense Mutations

The human genome contains a number genes for CGA-arginine t-RNAs. These are very compact genes and contain intragenic promoters for RNA polymerase III (Lewin B., In: Genes VII, Oxford University Press, 2000, pp. 624-626). Two of these genes, which for convenience, were designated TR3 and TR4B, were identified in the current assembly of the human genome (HG17; http://genome.ucsc.edu) and were amplified from normal human control DNA. TR3 is located on chromosome 6p22.1 and TR4B is located on chromosome 15q26.1. Specifically, the TR3 gene was amplified as a 668 by fragment using primers TR3.F 5' CGA TGC AGA CAA TAT GCA GA 3' and TR3.R 5' CTA AGC CTA CAA AAC CGA AA 3', corresponding to base numbers chr6:26,407,555-26,408,284 in the HG17 assembly of the human genome. The TR4B gene was amplified as a 465 by fragment using primers TR4B.F 5' GAC TTC TGG GTG GGC TCT CC 3' and TR4B.R 5' CCC TCC CTC TCC ACT TTC CT 3'. This fragment corresponds to base numbers chr15:87,679,164-87,679,628 in the HG17 assembly of the human genome. PCR was performed using the High-fidelity PCR system (Roche) and the following conditions: (94° C. 2 min)×1; (94° C. 30 sec, X° C. 30 sec, 72° C. 60 sec)×35; (72° C. 5 min)×1. For TR3, annealing temperature X=55° C.; for TR4B, X=58° C. These fragments were cloned into the pCR2.1 vector (InVitrogen) and several clones sequenced to obtain a clone of each construct free from PCR cloning artefacts. Annotated sequences of the complete constructs are shown in FIGS. 3 & 4. The predicted secondary structures for the resultant tRNA molecules are shown in FIG. 5. The anticodon loops of these tRNA genes were mutated so that these would recognize the TGA stop codon instead of the CGA arginine codon, i.e. the anticodon loop in the gene was mutated from 5' TCG 3' to 5' TCA 3'. In the TR3 gene, this corresponded to the mutation G351A, arbitrarily numbering from the first base of primer TR3.F (above). In TR4B, this mutation corresponded to G180A, numbering from the first base of primer TR4B.F (above).

EXAMPLE 3

Dual Luciferase Assay for FLG Readthrough

Co-reporter constructs pRLF-FLG-WT and pRLF-FLG-501X were tested by transient transfection into 293 cells (transformed human kidney epithelial cell line) using the Fugene-6 system (Roche) in 96-well plates. At 48 hours post-transfection, cells were subjected to the Dual luciferase assay system (Promega) which detects specific luciferase signals corresponding to both Renilla and Firefly luciferase reporter genes. With the wild-type co-reporter, pRLF-FLG-WT, a strong signal was obtained for both Renilla and Firefly luciferases, as shown in FIG. 6a. In contrast, only a Renilla signal was obtained with the pRLF-FLG-501X construct, showing that the R501X premature termination codon mutation present within the FLG cassette in this construct leads to complete loss of Firefly luciferase expression (FIG. 6a).

EXAMPLE 4

Readthrough Assay for FLG Nonsense Mutations

Transient transfections of 293 cells were done in 96-well plates as described above, using pRLF-FLG-501X with a range of gentamicin concentrations from 0 to 2000 µg/ml. Positive control transfections were done in parallel using pRLF-FLG-WT. Filaggrin nonsense mutation readthrough activity was measured using the Dual-luciferase assay system (Promega), as described above. FIG. 6b shows that gentamicin allows read-though of the R501X premature termination codon mutation in a dose-dependent manner, with maximum readthrough at a concentration of 2000 µg/ml in this experiment. As an alternative to using aminoglycosides for readthrough of the R501X mutation, human suppressor transfer-RNA (tRNA) species TR3supTGA and TR4BsupTGA were tested (see Example 2). These were co-transfected into 293 cells with the pRLF-FLG-501X reporter plasmid described above using the Fugene-6 transient transfection system (Roche). This showed that both suppressor tRNA species tested gave a strong read-through signal (FIG. 6b).

EXAMPLE 5

Reactivation of Filaggrin Expression in Keratinocyte Culture

Primary keratinocyte cultures were established from an individual with severe IV, who had been shown to be homozygous for the filaggrin R501X mutation, as described in Smith F J D et al., Nature Genetics 2006, in press. Normal primary keratinocytes do not express filaggrin to appreciable levels since the latter is a late-differentiation specific protein. However, these cells can be induced to express filaggrin by shifting the cultures to high-calcium medium, which causes stratification and differentiation of keratinocytes, leading to expression of filaggrin (Smith F J D et al., 2006 in press). Differentiation of normal, control keratinocytes lead to profilaggrin expression in colonies of cells that were well-stratified (FIG. 7). The protein was stained using indirect immunofluorescence with monoclonal antibody 15C10 (Novocastra) against an epitope in the human filaggrin repeat peptide. In contrast, well-stratified cultures from the R501X homozygote patient failed to express profilaggrin (FIG. 7, see also Smith F J D et al., 2006, in press). However, when the differentiated cultures from the R501X homozygote patient were treated with 600 µg/ml gentamicin, well-stratified colonies of cells were seen to express profilaggrin at levels comparable to the normal control, at 96 hours (FIG. 7). Furthermore, the profilaggrin was present in the form of cytoplasmic granules, comparable to those seen in control keratinocytes. Thus, gentamicin is able to facilitate read-through of the R501X filaggrin mutation in cultured cells.

EXAMPLE 6

Reactivation of Epidermal Filaggrin Expression in Organ Culture 3 mm cubes of skin biopsy material from a filaggrin R501X/R501X homozygous patient with marked IV were incubated in Dulbecco's modified Eagle medium for 4 days in culture, plus or minus 600 µg/ml gentamicin. Following incubation, the biopsy material was fixed and embedded for histology and immunohistochemistry. The untreated biopsy was completely negative when stained with monoclonal antibody 15C10 (Novacastra) against an epitope in the human filaggrin repeat peptide (FIG. 8), consistent with homozygosity for filaggrin null mutations (Smith F J D et al., Nature Genetics paper, 2006, in press). In contrast, the biopsy material incubated with gentamicin showed intense staining of the granular cell layers (FIG. 8). Absence of histologically identifiable keratohyalin granules is the hallmark of severe IV due to homozygous or compound heterozygous filaggrin null mutations (Smith F J D et al., Nature Genetics paper, 2006, in press). Significantly, the recovery of filaggrin staining seen here with gentamicin treatment, leads to the de novo appearance of keratohyalin granules (FIG. 8). Furthermore, in some cells high in the granular layer, where filaggrin staining is particularly intense, the cell morphology is seen to become more flattened (FIG. 8). Thus, the recovered protein expression appears to facilitate the correct terminal differentiation of the epidermis, consistent with full recovery of filaggrin protein function.

References

1. Wells, R. S. and Kerr C B, Br Med J., 1:947-949 (1966).
2. Judge, M. R., McLean, W. H. I. & Munro, C. S. Disorders of keratinization, in Rook's Textbook of Dermatology, Vol. 2 (eds. Burns, T., Breathnach, S., Cox, C. & Griffiths, C.) 34.54-34.56 (Blackwell Scientific Publishing, Oxford, 2004).
3. Steinert, P. M., Cantieri, J. S., Teller, D. C., Lonsdale-Eccles, J. D. & Dale, B. A. Characterization of a class of cationic proteins that specifically interact with intermediate filaments. Proc Natl Acad Sci 78, 4097-4101 (1981).
4. Dale, B. A., Resing, K. A. & Lonsdale-Ecccles, J. D. Filaggrin: a keratin filament associated protein. Ann. NY Acad. Sci. 455, 330-342 (1985).
5. Listwan, P. & Rothnagel, J. A. Keratin bundling proteins. Methods Cell Biol 78, 817-27 (2004).
6. Gan, S. Q., McBride, O. W., Idler, W. W., Markova, N. & Steinert, P. M. Organization, structure, and polymorphisms of the human profilaggrin gene. Biochemistry 29, 9432-40 (1990).
7. Candi, E., Schmidt, R. & Melino, G. The cornified envelope: a model of cell death in the skin. Nat Rev Mol Cell Biol 6, 328-40 (2005).
8. Fleckman, P., Holbrook, K. A., Dale, B. A. & Sybert, V. P. Keratinocytes cultured from subjects with ichthyosis vulgaris are phenotypically abnormal. J Invest Dermatol 88, 640-5 (1987).
9. Pena Penabad, C. et al. Differential patterns of filaggrin expression in lamellar ichthyosis. Br J Dermatol 139, 958-64 (1998).

10. Sybert, V. P., Dale, B. A. & Holbrook, K. A. Ichthyosis vulgaris: identification of a defect in synthesis of filaggrin correlated with an absence of keratohyaline granules. *J Invest Dermatol* 84, 191-4 (1985).
11. Nirunsuksiri, W., Zhang, S. H. & Fleckman, P. Reduced stability and bi-allelic, coequal expression of profilaggrin mRNA in keratinocytes cultured from subjects with ichthyosis vulgaris. *J Invest Dermatol* 110, 854-61 (1998).
12. Presland, R. B. et al. Loss of normal profilaggrin and filaggrin in flaky tail (ft/ft) mice: an animal model for the filaggrin-deficient skin disease ichthyosis vulgaris. *J Invest Dermatol* 115, 1072-81 (2000).
13. Smith, F. J. D. et al. "Loss-of-function mutations in the filaggrin gene cause ichthyosis vulgaris", Nature Genetics, 2006, in press.
14. Palmer C. N. A. et al. "Haploinsufficiency for the epithelial barrier protein filaggrin is a major predisposing factor for asthma and atopic dermatitis", submitted.
15. Presland, R. B. et al. Evidence for specific proteolytic cleavage of the N-terminal domain of human profilaggrin during epidermal differentiation. *J Invest Dermatol* 108, 170-8 (1997).
16. Ishida-Yamamoto, A., Takahashi, H., Presland, R. B., Dale, B. A. & Iizuka, H. Translocation of profilaggrin N-terminal domain into keratinocyte nuclei with fragmented DNA in normal human skin and loricrin keratoderma. *Lab Invest* 78, 1245-53 (1998).
17. Lane, P. W. Two new mutations in linkage group XVI of the house mouse. Flaky tail and varitint-waddler-J. *J Hered* 63, 135-40 (1972).
18. Rothnagel, J. A. et al. Characterization of the mouse loricrin gene: linkage with profilaggrin and the flaky tail and soft coat mutant loci on chromosome 3. *Genomics* 23, 450-6 (1994).

The invention claimed is:

1. A method of treating ichthyosis vulgaris ("IV") comprising the step of administrating to a subject an antibiotic agent or tRNA, wherein the antibiotic agent or tRNA is capable of enabling read-through of a loss-of-function mutation in a filaggrin gene.

2. The method according to claim 1, wherein the loss of function mutation is a nonsense mutation.

3. The method according to claim 2, wherein the mutation is 1501C>T (numbering from initiating ATG), which results in the substitution of a cytidine by a thymidine and a corresponding amino acid change at position 501 of an arginine to stop codon (R501X).

4. The method according to claim 1, wherein the subject is a neonate, child or adult.

5. The method according to claim 1, wherein the antibiotic agent is an aminoglycoside antibiotic.

6. The method according to claim 5, wherein the aminoglycoside is gentamicin, paromomycin, neomycin or tobramycin.

7. The method according to claim 1, wherein the antibiotic agent is negamycin.

8. The method according to claim 1, wherein the tRNA is a mutant tRNA.

9. The method of testing an agent for its ability to read-through a nonsense mutation for use in treating ichthyosis vulgaris ("IV") comprising steps of:
   a) contacting a test agent with a mutant filaggrin gene/reporter gene construct; and
   b) detecting whether or not the test agent is capable of effecting read-through of the mutant filaggrin gene and expression of a reporter gene.

10. The method according to claim 9 wherein the filaggrin nucleic acid sequence is 10-1000 bp in length.

11. The method according to claim 9 wherein the mutant filaggrin gene/reporter gene construct comprises a 5' mutant filaggrin nucleic acid sequence joined in-frame to a 3' reporter gene sequence.

12. The method according to claim 11 wherein the construct further comprises an additional positive control reporter gene 5' of the filaggrin sequence.

13. The method according to claim 12 wherein the additional reporter gene is selected from the group consisting of: a luciferase gene, a β-galactosidase gene, a gene encoding a green fluorescent protein, a chloramphenicol acetyltransferase gene, and a β-glucuronidase gene.

14. A method according to claim 13 wherein the construct is as schematically shown in FIG. 1.

* * * * *